(12) United States Patent
Hudak

(10) Patent No.: US 6,774,993 B2
(45) Date of Patent: Aug. 10, 2004

(54) METHOD AND APPARATUS FOR ATOMIC EMISSION SPECTROSCOPY

(75) Inventor: George J. Hudak, Kennett Square, PA (US)

(73) Assignee: Agilent Technologies, Inc., Palo Alto, CA (US)

( * ) Notice: Subject to any disclaimer, the term of this patent is extended or adjusted under 35 U.S.C. 154(b) by 63 days.

(21) Appl. No.: 09/825,048

(22) Filed: Apr. 3, 2001

(65) Prior Publication Data

US 2003/0214651 A1 Nov. 20, 2003

(51) Int. Cl.[7] .................................................. G01J 3/30
(52) U.S. Cl. .................................................... 356/316
(58) Field of Search ......................... 356/36, 306, 307, 356/311, 316, 317, 318, 326, 328, 330; 73/23.2, 31.05

(56) References Cited

U.S. PATENT DOCUMENTS

| | | | |
|---|---|---|---|
| 4,257,001 A | * 3/1981 | Partain et al. | 324/636 |
| 4,598,577 A | * 7/1986 | Jowitt et al. | 356/36 |
| 4,654,504 A | 3/1987 | Sullivan et al. | 219/121 |
| 5,179,264 A | * 1/1993 | Cuomo et al. | 219/121.43 |
| 5,452,069 A | * 9/1995 | Arnold et al. | 356/316 |
| 5,506,678 A | 4/1996 | Carlsen et al. | 356/338 |
| 5,521,703 A | 5/1996 | Mitchell | 356/301 |
| 5,526,110 A | * 6/1996 | Braymen | 250/252.1 |
| 5,597,495 A | * 1/1997 | Keil et al. | 156/345.39 |
| 5,673,109 A | 9/1997 | Keilbach | 356/301 |
| 5,844,149 A | * 12/1998 | Akiyoshi et al. | 73/864.81 |
| 5,929,981 A | 7/1999 | Keilbach | 356/73 |
| 5,986,757 A | * 11/1999 | Seltzer | 356/307 |
| 6,093,921 A | 7/2000 | Gaisford et al. | 219/748 |
| 6,577,390 B1 | * 6/2003 | Efthimion | 356/316 |

OTHER PUBLICATIONS

Saleh et al, Fundamentals of Photonics, 1991, Jon Wiley & Sons, Inc., pp. 476–477.*
Saleh et al, Fundamentals of Photonics, 1991, Jon Wiley & Sons, Inc., pp. 476–477.*

* cited by examiner

Primary Examiner—Euncha P. Cherry

(57) ABSTRACT

A gas plasma emission source includes a solid state signal power source coupled to a resonant cavity. In an alternative embodiment of the invention, an atomic emission detector includes a solid state signal power source coupled to a resonant cavity and a spectrographic detector to sense atomic emissions from a gas within the resonant cavity. In yet another embodiment of the invention, a method of sustaining a plasma includes passing a gas through a resonant cavity and exciting the resonant cavity with signal power from a solid state power source to sustain the plasma in the gas. In another embodiment of the invention, a method of using a solid state power source includes passing a gas through a resonant cavity and coupling sufficient signal power from an output of the solid state power source to sustain a plasma in the gas where the sufficient power is less than 300 watts.

17 Claims, 4 Drawing Sheets

METHOD AND APPARATUS FOR ATOMIC EMISSION SPECTROSCOPY

BACKGROUND OF THE INVENTION

1. Field of the Invention

The present invention relates to a gas spectrometer. In particular, the invention relates to a method and apparatus for exciting a plasma in a gas for use in the gas spectrometer.

2. Description of Related Art

Detection and monitoring of gases are of great importance in many applications. For example, often a laboratory instrument to measure gases is required. Harmful fumes can be emitted from industrial site containers (e.g., plating and etching baths). Dangerous gases may be emitted in mines, or anaesthesia gases may fill a surgical operating room. To detect such gases and monitor their concentration, known spectrometers employ an instrument that uses the physical phenomenon known as Raman scattering. Such instruments have a laser that directs an intense beam through a chamber containing a sample of the gas to be measured. The sample gas produces a weak stimulated emission that is frequency (i.e., wavelength) shifted from the original stimulating laser beam. The magnitude of this frequency shift is dependent on the sample gas type.

There are several patents that describe improvements to the methods of measuring Raman scattering. U.S. Pat. No. 5,929,981 to Keilback describes a system for monitoring contamination of optical elements in a Raman gas analyzer. U.S. Pat. No. 5,673,109 to Keilback describes a system and method for increasing the efficiency of a Raman gas analysis system. U.S. Pat. No. 5,521,703 to Mitchell describes a diode laser pumped Raman gas analysis system with reflective hollow tube gas cell. U.S. Pat. No. 5,506,678 to Carlsen et al. describes a system for collecting weakly scattered electromagnetic radiation for a Raman gas analysis system.

Known gas chromatographic analyzers pass a gas mixture down a column where individual gases in the gas mixture adsorb and release from the column walls at different rates. The temperature at which the column walls are maintained will often alter the rate at which particular gases adsorb to the walls. U.S. Pat. No. 6,093,921 to Gaisford et al. describes a microwave heating apparatus for gas chromatographic columns to achieve a controlled temperature profile along the length of the column.

In the background to U.S. Pat. No. 4,654,504 to Sullivan, et al., there is described a detector in which a gas containing chemical compounds to be analyzed is passed through a tube mounted within a resonant cavity that is powered by magnetron of the type used in a microwave oven for the home. U.S. Pat. No. 4,654,504 to Sullivan, et al., incorporated herein by reference, goes on to describe the cooling of the discharge tube by flowing a coolant into thermal communication with an outside surface of the discharge tube so as to reduce the erosion of the inner surface of the discharge tube and attain a satisfactory discharge tube life.

However, known analysis systems that analyze the gases out of such gas chromatographic systems do not have a solid-state signal power source that sustains the gas in a plasma state for the analysis of the spectra of the light emitted from the plasma.

SUMMARY OF THE INVENTION

It is an object to the present invention to provide an emission source with a long life discharge tube. It is another object of this invention to provide a solid state power source for a signal that sustains a plasma in an emission source. It is a further object of the present invention to provide an emission source within a discharge tube sustained by a low cost simple solid-state signal power source.

These and other objects are achieved in a gas plasma emission source that includes a solid state signal power source coupled to a resonant cavity.

Alternatively, these and other objects are achieved in an atomic emission detector that includes a solid state signal power source coupled to a resonant cavity and a spectrographic detector to sense atomic emissions from a gas within the resonant cavity.

In another alternative embodiment, these and other objects are achieved with a method of sustaining a plasma that includes passing a gas through a resonant cavity and exciting the resonant cavity with signal power from a solid state power source to sustain the plasma in the gas.

In yet another embodiment of the invention, these and other objects are achieved with a method of using a solid state power source that includes passing a gas through a resonant cavity and coupling sufficient signal power from an output of the solid state power source to sustain a plasma in the gas where the sufficient power is less than 300 watts.

BRIEF DESCRIPTION OF DRAWINGS

The invention will be described in detail in the following description of preferred embodiments with reference to the following figures wherein.

DETAILED DESCRIPTION OF PREFERRED EMBODIMENTS

Figure 5:
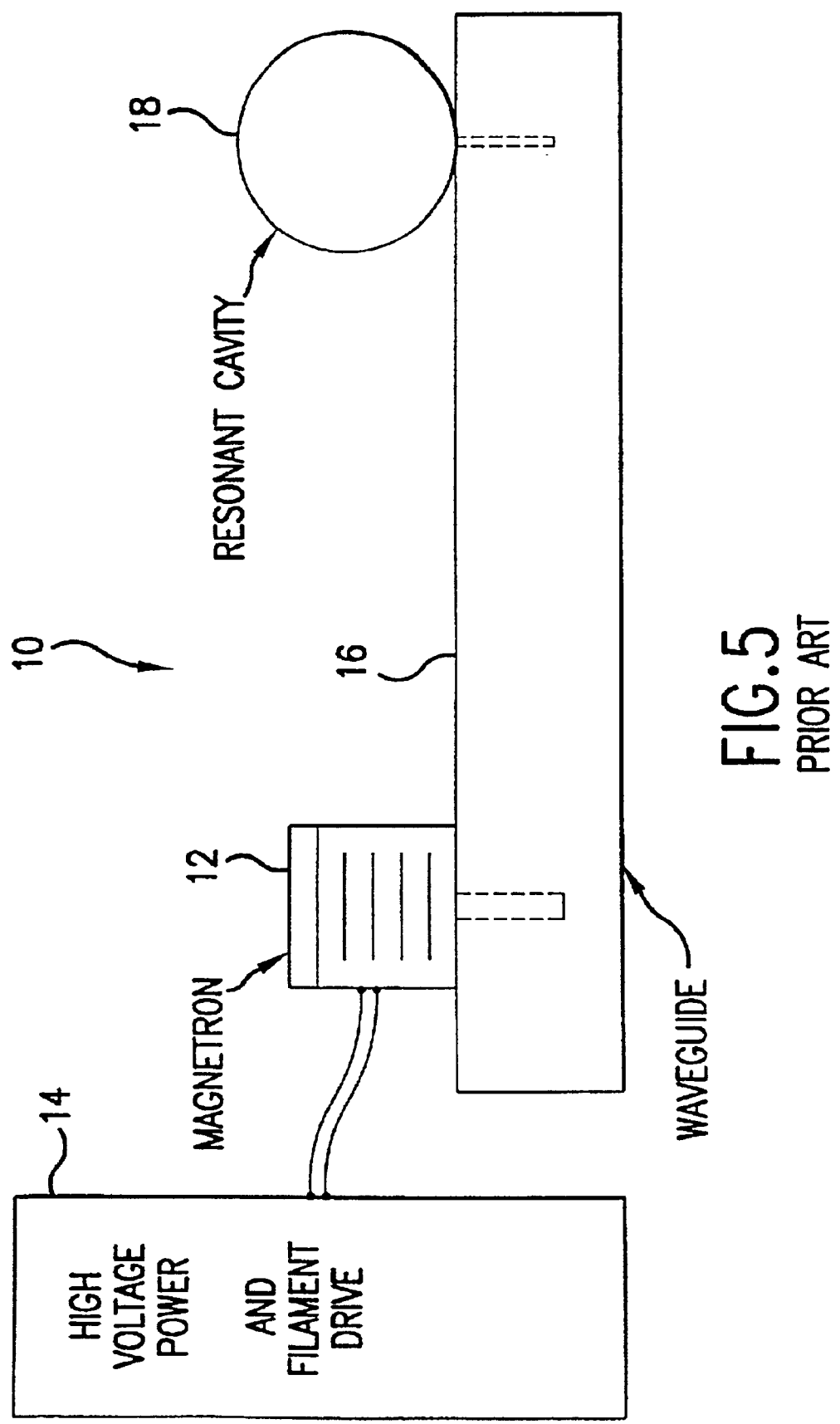
FIG. 5 is a schematic block diagram of a known circuit for exciting a plasma using a magnetron.

In FIG. 5, gas spectrometer 10 includes magnetron 12, powered from power source 14, to generate microwave signals at high power. The microwave output of magnetron 12 propagates down waveguide 16 to excite a resonance in cavity resonator 18. Typically, magnetrons from microwave ovens are used as a signal source to sustain a gas in a plasma state as an emission source for a spectrometer. Such magnetrons and associated power supply are relatively inexpensive (e.g., under $1000) and typically generate continuous wave (CW) microwave power levels between 500 watts and 1000 watts.

However, magnetron 12 uses vacuum tube technology that requires a high current source to drive a filament heater in the magnetron and a high voltage source for the magnetron electrodes. Power source 14 provides these power requirements.

Figure 1:
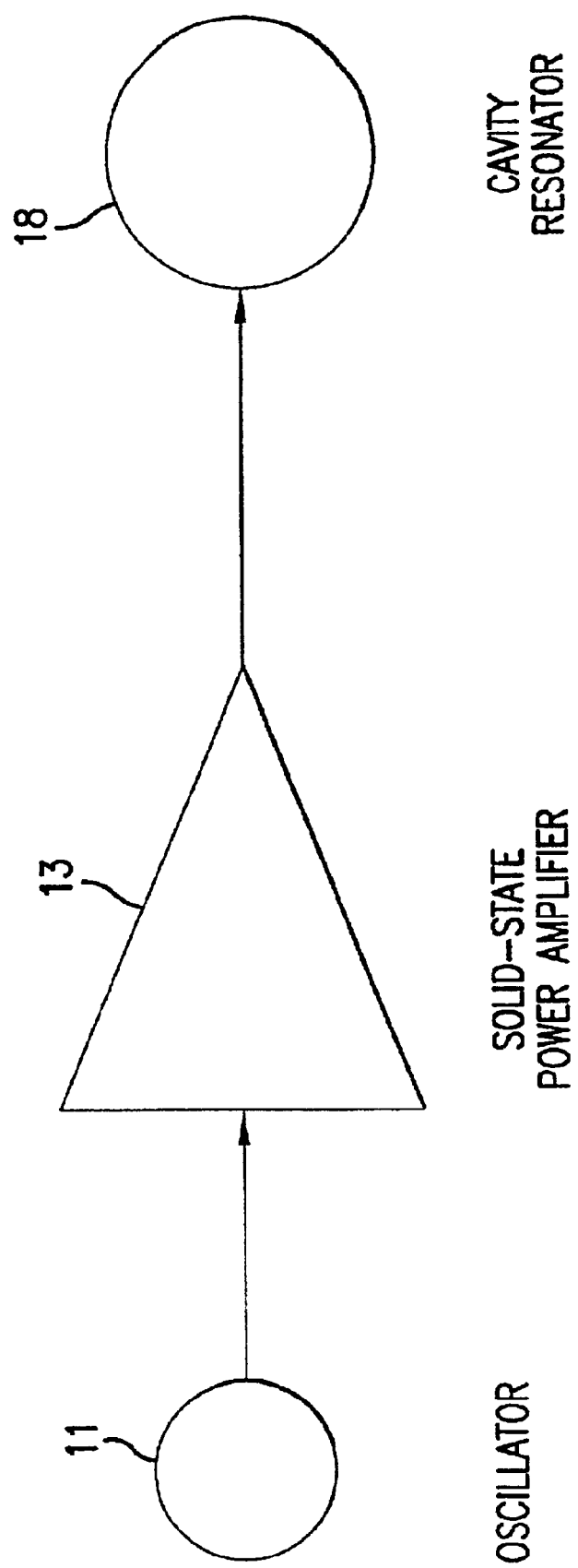
FIG. 1 is a schematic block diagram of a circuit for exciting a plasma according to the present invention.

In FIG. 1, oscillator 11 and solid-state power amplifier 13 form a solid state signal power source to replace magnetron 12 of FIG. 5. A simpler, low voltage power supply (not shown) may be used to replace power supply 14 which had been made larger and more complicated by the need to power a magnetron.

Moreover, stable signal power delivered as a continuous wave (CW) by solid-state power amplifier 13 may be provided at any desired frequency (e.g., a frequency selected to match the resonant frequency of resonant cavity 18) and typically at 2,450 MHz or 915 MHz in the ISM bands (industrial, scientific and medical bands). An advantage of a solid state power source is that the power source (11, 13) can easily provide signal power at frequencies over a wide band of frequencies. This avoids instability that may arise from an interaction between the resonant frequency of cavity 18 and a resonant cavity within a magnatron. Magnatrons are inherently narrow band devices (although some can tune their frequency within a narrow band). Solid-state power amplifier 13 can deliver the signal power at any desired signal power level over wide dynamic range, and in particular, at power levels well below the levels at which a microwave oven magnetron can deliver stable signal power. Any solid state technology may be used to generate the signal power source, for example, silicon based or gallium arsenide based technology are currently popular. Another advantage of the solid state power source is that it may provide signal power at any desired power level, and in particular, a lower power levels that merely sustain a plasma without burning up a discharge tube (as discussed below). Solid-state power amplifier 13 can easily provide signal power at power levels of 25 watts, 50 watts, or 100 watts. This provides advantages as discussed below. In fact, oscillator 11 and solid state power amplifier 13 need not be distinct and separate circuits. When required signal power levels are available at the desired frequency in a single circuit, the single circuit may be substituted for oscillator 11 and solid state power amplifier 13.

Several years ago such a solid-state power amplifier would cost over $50,000, and this would raise the price of a gas spectrometer of this type to unacceptable levels. However, recent emphasis on the use of solid-state technology for radios in the industrial, scientific, medical band (i.e., the ISM band) has led to suitable solid-state power amplifiers in the $1,000 range.

The fall in the cost of solid-state amplified 13 has made the circuit of FIG. 1 economically feasible for application in a gas spectrometer. The circuit of FIG. 1 overcomes several of the limitations experienced by the magnetron based circuits (e.g., FIG. 5) in unique ways. One of the advantages of the circuit of FIG. 1 over the circuit of FIG. 5 is the simpler, and therefore less expensive, power supply needed to power the signal power source. Another advantage is that signal power may be provided at lower power levels (e.g., power levels less than 300 watts) with a stable output power level and a low impedance signal source of FIG. 1. In contrast, magnetrons made for the microwave oven market, as well as other magnetrons, operate with poor stability at power levels less than 300 watts. For reasons discussed herein, the signal power source for a gas spectrometer is preferred to be operated at less than 300 watts. Among the reasons to prefer the lower power operation is that a discharge tube has a longer working life at lower powers as discussed further herein.

The signal output of solid-state power amplifier 13 is coupled to cavity resonator 18. Typically, cavity resonator 18 is a cylindrical metallic cavity resonator designed to resonate at the frequency of the output signal of solid state power amplifier 13. However, cavity 18 may be of any resonant shape (e.g., a box like the inside of a microwave oven). Another advantage of the use of oscillator 11 and solid state power amplifier 13 over a magnetron is that resonant cavity 18 may be manufactured with relaxed tolerances when oscillator 11 can be tuned to seek the resonant frequency of cavity 18. By tuning oscillator 11 to the resonant frequency of cavity 18, a lower signal power (from solid state amplifier 13) may be used to sustain the plasma. In fact, since the solid state power source is frequency tunable over a wide band of frequencies, the dimensions of cavity 18 maybe arbitrarily selected and the frequency of oscillator 11 tuned to match cavity 18. Magnetron frequencies are defined by the frequency of an internal magnetron resonant cavity which ordinarily cannot be tuned over a wide frequency range. Thus, magnetrons are not generally tuneable to the frequency at which cavity 18 resonates.

Figure 2:
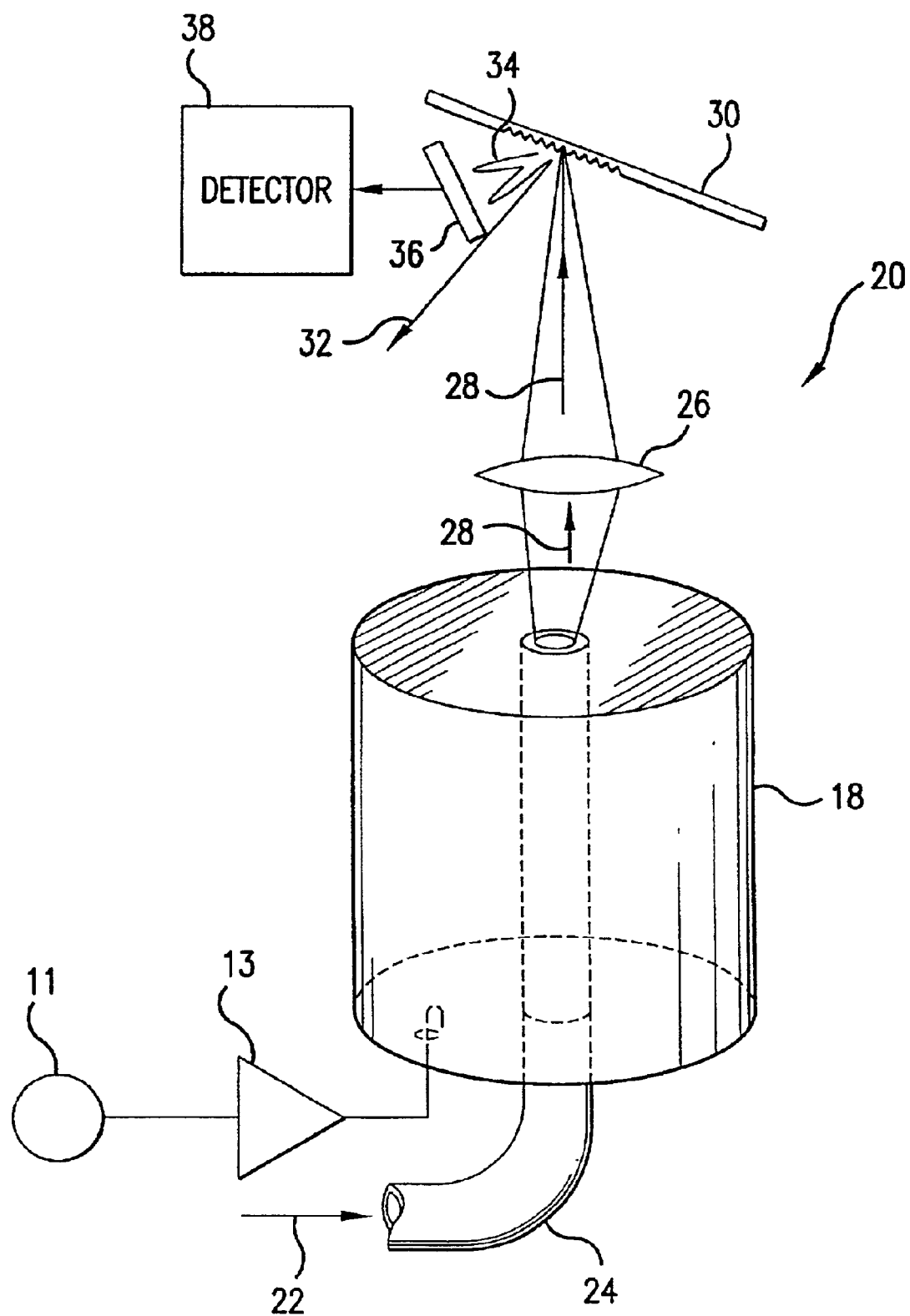
FIG. 2 is a perspective view and schematic diagram of a spectrographic detector.

In FIG. 2, atomic emission spectrometer 20 includes cavity resonator 18 with a central axis through its center. Gas discharge tube 24 is disposed co-linear with this central axis. Discharge tube 24 carries gas 22 through the center of cavity resonator 18. Signal power from solid-state power amplifier 13 is coupled into cavity resonator 18, typically through a coaxial cable. The exact coupling point depends on the resonant mode to be excited in cavity resonator 18, and persons skilled in the art will appreciate how to determine the coupling point in light of these teachings.

The use of a coaxial cable has several advantages. Among these are that the coaxial coupling is more flexible than waveguides and often easier to assemble. However, waveguide coupling is favored when the power to be coupled is above 300 watts. At higher powers, the losses in coaxial cables and connectors become more of a problem. For at least this reason, the use of a coaxial cable is preferred in lower power applications. The use of oscillator 11 and solid-state power amplifier 13 to provide stable signal power, enables the emission source to be operated at a lower sustaining signal power, and this in turn, enables the use of coaxial coupling.

Gas 22 passes through discharge tube 24 and typically exits an open end of the tube after it has passed through the central part of cavity resonator 18. When a resonant mode has been achieved in cavity resonator 18, oscillating electric fields pass at peak amplitude (i.e., at are sonant frequency) through gas 22 located within discharge tube 24 in the center of cavity resonator 18. These fields are adjusted to be almost strong enough to ignite a plasma, and certainly strong enough to sustain a plasma.

A pair of points (not shown) are preferably disposed in discharge tube 24 and driven by a sparking generator such as may be used in a conventional automobile spark plug ignition system. The sparking generator supplies sufficient additional electric field to the gases between the points in discharge tube 24 to ignite a plasma. At this point, the oscillating electric fields excited in cavity 18 by solid state power amplifier 13 are sufficiently strong that gas 22 located within discharge tube 24 in the center of cavity resonator 18 turns into a heated plasma that emits light at a wavelength that indicates the type of gaseous material and at an intensity that indicates the quantity of the gaseous material in the plasma.

The light that emits from discharge tube 24 propagates generally along axis 28 and is focused by lens 26 onto diffraction grating 30. Diffraction grating 30 is oriented to generally reflect light impinging from axis 28 (at an angle of incidence) into an angle of reflection along axis 32. However, the diffraction grating further diffracts the light at an angle that depends on the wavelength of the emitted light as represented by diffraction pattern 34. Linear photo-diode array 36, or an equivalent sensor, is disposed to intercept and measure the diffracted light. The intercepted light is captured as photo charge by sensor array 36. The photo charged capture by any photo-diode is proportional to the intensity of the intercepted light. The particular photo-diode measured corresponds to angle of diffraction, and hence, indicates the wavelength. Linear photo-diode array 36 is read out into detector circuit 38 for further processing.

Typically, inexpensive magnetrons, as used in microwave ovens, deliver 500 to 1000 watts of continuous wave microwave power. This power level exceeds the requirements of an emission source for the subject spectroscope. This power level leads to premature consumption (e.g., burn out) of discharge tube 24.

Discharge tube 24 is typically made from either fused silica or sapphire. Sapphire is very tough and resists the high temperatures that are present in a plasma as discussed herein. However, sapphire is not quite as chemically inert as desired. The plasma of certain gases will tend to interact and possibly etch away material from the walls of discharge tube 24, and this erosion leads to a premature end of life for the discharge tube.

On the other hand, fused silica is more chemically inert, but it does not withstand the high temperatures of a plasma as well as sapphire. The high temperatures in the plasma will melt the walls of the discharge tube and lead to a premature end of life for the discharge tube.

Figure 3:
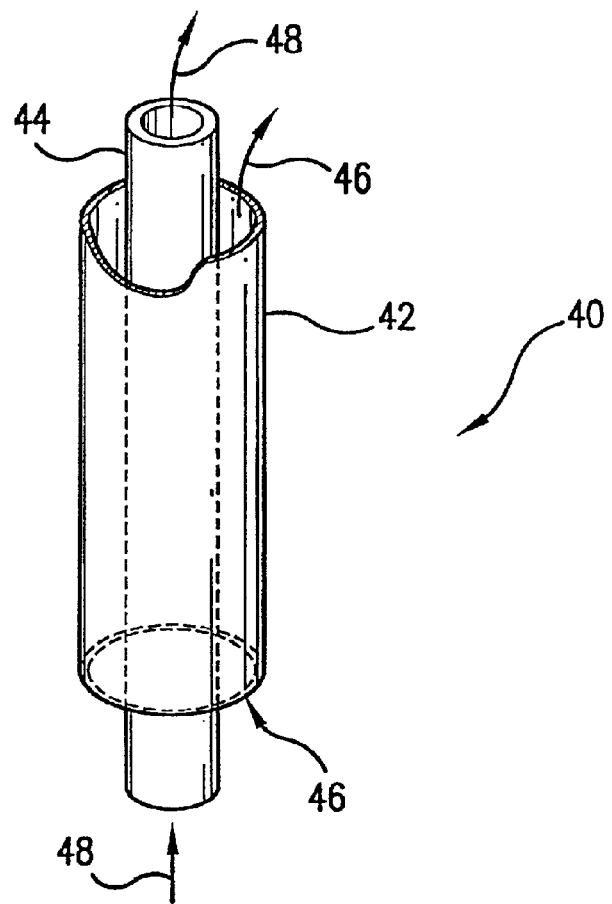
FIG. 3 is a perspective view and schematic diagram of an improved discharge tube.

In FIG. 3, improved discharge tube 40 is an example of a replacement for ordinary discharge tube 24. Improved discharge tube 40 includes outer jacket 42 and inner tube wall 44. Between outer jacket 42 and inner tube wall 44 water 46 flows to cool inner tube wall 44. Through the interior of the tube formed by inner tube wall 44, gas 48 flows, the plasma of which is to be analyzed.

The advantage of this arrangement is that inner tube wall 44 can be formed from the more chemically inert fused silica. The water flow cools inner tube wall to extend the working life of the discharge tube to make this improved tube practical. However, the compound nature of improved discharge tube 40 is more costly to begin with.

In the improved discharge tube 40, the inner tube wall is disposed in the center of cavity resonator 18. The plasma of the heated gas to be analyzed is in the center of inner tube wall. The plasma absorbs signal energy from cavity resonator 18. Similarly, water between outer jacket 42 and inner tube wall 44 of improved discharge tube 40 absorbs signal energy from cavity resonator 18.

Figure 4:
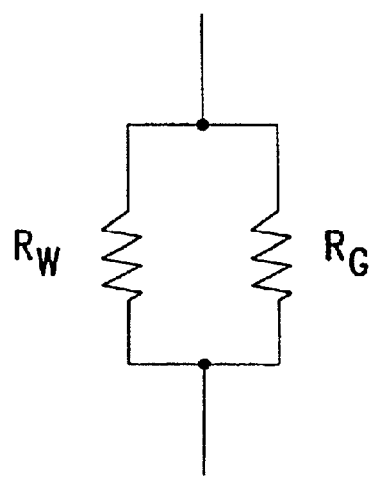
FIG. 4 is an equivalent circuit schematic diagram of the plasma and discharge tube of FIG. 3.

FIG. 4 is a circuit schematic illustrating an equivalent circuit of the two loads on the resonance of cavity resonator 18. The water load is represented by resistor $R_w$, and the gas plasma load is represented by the $R_G$. The two resistive loads (i.e., lossy loads) are in parallel.

At least the gas plasma component of the combined impedance load in the cavity resonator will tend to fluctuate randomly as might be expected in a plasma. This phenomenon results in a fluctuating load on the source of microwave power.

Magnetrons, like most vacuum tube electronic devices, are high impedance devices (i.e., operate with higher voltages and lower currents relative to solid-state devices), at least high impedance relative to the cavity resonator load. When the cavity resonator load impedance fluctuates (e.g., as a result of the fluctuating plasma), magnetron 12 must drive a fluctuating load, and the magnetron bias point fluctuates accordingly. The power output and frequency of the magnetron fluctuates as well, which contributes to further instability of the plasma. The fluctuating unstable plasma appears as a modulated light signal to the spectrometer, and it adds noise to the light measured by the spectrometer.

With magnetrons as the signal source, the signal output power level is important. The magnetrons that are used in microwave ovens are the most economical source of magnetrons; however, these magnetrons produce signal power at about 500 watts. It is quite difficult to adjust a magnetron to produce continuous wave signal power below 300 watts. Pulsed magnetrons are unacceptable because the pulses contributed to the plasma instability and noise floor of the eventual measurement.

A practical lower limit to CW magnetron power is about 300 watts. Below this power level, the magnetron becomes unstable in frequency and/or power output. This signal power level produces a plasma that is so hot that it tends to prematurely burn out the discharge tube. Fused silica discharge tubes simply melt when the plasma is operated too hot, but the fused silica is relatively inert (e.g., contributing only oxygen and silicon atomic emission lines to the spectrometer measurement). Sapphire discharge tubes better resist the high temperatures, but interact with the plasma causing chemical interference. An improved water jacketed discharge tube such as tube 40 (FIG. 3) may be used to cool a fused silica discharge tube to extend its useful life, but the complexity of the improved discharge tube adds to the cost of the spectrometer.

The present invention uses a solid-state signal power source (e.g., oscillator 11 and solid-state power amplifier 13) to provide a tuneable and lower signal power to excite resonance in cavity 18 to sustain the plasma. For example, a suitable plasma may be developed with as little as 25 watts, or 50 watts or 100 watts. Attempting to operate a magnetron at these lower levels leads to an unstable power level that raises the noise floor in the spectrometer measurement. Furthermore, the solid-state power source of the present invention (i.e., oscillator 11 and solid-state power amplifier 13) not only provides signal power at the desired power level, but the output impedance of solid-state power amplifier 13 is low so that fluctuating plasma loads do not materially effect the output power level.

The present novel emission source includes a solid state power source coupled to a resonant cavity such as cavity 18. Resonate cavity 18 has discharge tube 24 disposed through the resonant cavity. The solid state power source couples into resonant cavity 18 a low but sufficient signal power to sustain a plasma in a gas disposed within tube 24. Any excessive power in the excitation of cavity 18 to sustain the plasma merely causes the plasma to be too hot and leads to the premature end of life of discharge tube 24. The sufficient power is less than 200 watts, and may be less than 50 watts. The plasma, once excited, constitutes a fluctuating load on the solid state power source. However, the solid state power source is of such a low output impedance that the sufficient power, that is coupled into resonant cavity 18, is substantially stable with respect to the fluctuating load.

Having described preferred embodiments of a novel method and apparatus for atomic emission spectroscopy (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as defined by the appended claims and their equivalents.

Having thus described the invention with the details and particularity required by the patent laws, what is claimed and desired protected by Letters Patent is set forth in the appended claims.

What is claimed is:

1. A gas plasma emission source comprising:
   a resonant cavity;
   a tube disposed through the resonant cavity, the tube enclosing a sample under test; and
   a solid state power source coupled through a coaxial cable to the resonant cavity to excite resonant oscillations in the resonant cavity, the resonant oscillations exciting a plasma in the sample under test, the plasma constituting a fluctuating load on the solid state power source.

2. A gas plasma emission source according to claim 1, wherein the tube comprises one of a fused silica tube and a sapphire tube.

3. A gas plasma emission source according to claim 1, wherein:
   the tube is configured in the resonant cavity so that the sample under test enters one end of the tube, passes through the resonant cavity and exits an open end of the tube, a line between the plasma and the open end of the tube being unobstructed by walls of the tube; and
   the gas plasma emission source further comprises a spectrographic detector disposed to sense atomic emissions emitted from the open end of the tube.

4. A gas plasma emission source according to claim 3, wherein the tube comprises one of a fused silica tube and a sapphire tube.

5. A gas plasma emission source according to claim 1, wherein the solid state power source couples a power level into the resonant cavity sufficient to sustain the plasma, the power level being less than 100 watts, the power level being substantially stable with respect to the fluctuating load.

6. A gas plasma emission source comprising:
   a resonant cavity; and
   a solid state power source coupled to the resonant cavity, wherein the resonant cavity includes a tube disposed through the resonant cavity, the tube being configured so that a sample under test enters one end of the tube, passes through the resonant cavity and exits an open end of the tube.

7. A gas plasma emission source according to claim 6, wherein the tube comprises one of a fused silica tube and a sapphire tube.

8. A gas plasma emission source according to claim 6, further comprising a spectrographic detector disposed to sense atomic emissions emitted from the open end of the tube, wherein:
   a signal from the solid state power source excites a plasma in the sample under test; and
   a line between the plasma and the spectrographic detector through the open end of the tube is unobstructed by walls of the tube.

9. A gas plasma emission source according to claim 8, wherein the tube comprises one of a fused silica tube and a sapphire tube.

10. A gas plasma emission source according to claim 6, wherein the solid state power source couples a power level into the resonant cavity sufficient to sustain the plasma, the power level being less than 100 watts, the power level being substantially stable with respect to the fluctuating load.

11. A gas plasma emission source comprising a resonant cavity and a solid state power source coupled to the resonant cavity, wherein:
   the solid state power source couples into the resonant cavity a power level to sustain a plasma in a gas disposed within the resonant cavity, the power level being less than 300 watts;
   the plasma constitutes a fluctuating load on the solid state power source; and
   the power level is substantially stable with respect to the fluctuating load.

12. The emission source of claim 11, wherein the power level is less than 100 watts.

13. An atomic emission detector comprising:
   a resonant cavity;
   a solid state power source coupled to the resonant cavity to excite resonant oscillations in the resonant cavity; and
   a spectrogaphic detector disposed to sense atomic emissions from a gas within the resonant cavity, wherein:
   the resonant cavity has a tube disposed along an axis;
   the gas enters the tube from one end of the tube, another end of the tube being an open end; and
   the spectrographic detector is disposed to sense atomic emissions emitted from the open end.

14. An atomic emission detector comprising:
   a resonant cavity;
   a solid state power source coupled to the resonant cavity to excite resonant oscillations in the resonant cavity; and
   a spectrographic detector disposed to sense atomic emissions from a gas within the resonant cavity, wherein:
   the resonant cavity includes a tube disposed through the resonant cavity; and
   the tube comprises one of a fused silica tube and a sapphire tube.

15. An atomic emission detector comprising:
   a resonant cavity;
   a solid state power source coupled to the resonant cavity to excite resonant oscillations in the resonant cavity; and
   a spectrographic detector disposed to sense atomic emissions from a gas within the resonant cavity, wherein:
   the solid state power source is coupled to the resonant cavity to provide a power level to sustain a plasma in the gas within the tube, the power level being less than 300 watts;
   the plasma constitutes a fluctuating load on the solid state power source; and
   the power level is substantially stable with respect to the fluctuating load.

16. The detector of claim 15, wherein the power level is less than 100 watts.

17. A method of sustaining a plasma comprising steps of:
   passing a gas through a resonant cavity;
   exciting the resonant cavity with signal power from a solid state power source to sustain the plasma in the gas; and
   directly observing the plasma with a spectrographic detector having an unobstructed view of atomic emissions from the plasma through an open end of a tube passing through the resonant cavity.

* * * * *